United States Patent
Imaizumi et al.

(10) Patent No.: US 7,450,159 B2
(45) Date of Patent: Nov. 11, 2008

(54) IMAGE PICK-UP APPARATUS AND ENDOSCOPE APPARATUS

(75) Inventors: Katsuichi Imaizumi, Hachioji (JP); Isami Hirao, Hachioji (JP); Yoshinori Takahashi, Hachioji (JP); Takeshi Ozawa, Sagamihara (JP); Sakae Takehana, Sagamihara (JP); Nobuyuki Doguchi, Hino (JP)

(73) Assignee: Olympus Corporation, Tokyo (JP)

( * ) Notice: Subject to any disclaimer, the term of this patent is extended or adjusted under 35 U.S.C. 154(b) by 682 days.

(21) Appl. No.: 10/977,654

(22) Filed: Oct. 29, 2004

(65) Prior Publication Data

US 2005/0117028 A1    Jun. 2, 2005

(30) Foreign Application Priority Data

Oct. 30, 2003    (JP) .............................. 2003-371117

(51) Int. Cl.
H04N 5/235    (2006.01)
H04N 5/238    (2006.01)
H04N 5/228    (2006.01)
H04N 9/73    (2006.01)

(52) U.S. Cl. ................. 348/222.1; 348/229.1; 348/363; 348/364; 348/224.1

(58) Field of Classification Search ................. 600/100, 600/180, 181, 178; 358/98, 168, 169; 128/6; 348/45, 65, 229, 255, 362, 363, 368, 300, 348/221.1, 225, 229.1

See application file for complete search history.

(56) References Cited

U.S. PATENT DOCUMENTS

| 4,532,918 | A | * | 8/1985 | Wheeler ..................... 600/109 |
| 4,803,550 | A | * | 2/1989 | Yabe et al. .................... 348/68 |
| 4,967,269 | A | | 10/1990 | Sasagawa et al. |
| 5,337,340 | A | | 8/1994 | Hynecek |
| 6,902,527 | B1 | * | 6/2005 | Doguchi et al. ............. 600/109 |
| 2003/0060684 | A1 | | 3/2003 | Ayame et al. |
| 2004/0143157 | A1 | * | 7/2004 | Doguchi et al. ............. 600/109 |
| 2005/0117028 | A1 | * | 6/2005 | Imaizumi et al. ......... 348/222.1 |
| 2007/0002134 | A1 | * | 1/2007 | Ishihara et al. ................ 348/65 |

FOREIGN PATENT DOCUMENTS

EP    1 099 405 A1    5/2001
JP    2002-336196    11/2002

* cited by examiner

Primary Examiner—Lin Ye
Assistant Examiner—Euel K Cowan
(74) Attorney, Agent, or Firm—Scully, Scott, Murphy & Presser, P.C.

(57) ABSTRACT

An image pick-up apparatus includes an image pick-up device which picks-up an image of a subject and outputs an image signal, a first-amplitude changing portion which varies an amplitude of the image signal outputted form the image pick-up device, a second-amplitude changing portion which varies the amplitude of the image signal to be outputted, a comparing portion which compares the amplitude of the image signal with a value of a target amplitude, and a control portion which controls the first- and second-amplitude changing portions based on the comparison result of the comparing portion and changes the amplitude of the image signal so that it is approximate to the target amplitude so that an observed image of the subject displayed on display means has a desired brightness.

17 Claims, 7 Drawing Sheets

IMAGE PICK-UP APPARATUS AND ENDOSCOPE APPARATUS

This application claims benefit of Japanese Application No. 2003-371117 filed in Japan on Oct. 30, 2003, the contents of which are incorporated by this reference.

BACKGROUND OF THE INVENTION

1. Field of the Invention

The present invention relates to an image pick-up apparatus and an endoscope apparatus having an image pick-up device whose amplification rate can be varied therein.

2. Description of the Related Art

Currently, an electronic endoscope is widely used for various therapeutic treatment processing which is performed by observing the trachea such as the lung or the gastrointestinal tract such as the esophagus, stomach, small intestine, and large intestine by inserting a scope in the body cavity with a treatment tool that is inserted in a treatment tool channel if necessary.

Recently, the auto-fluorescent observation is executed by using the auto-fluorescence of the living body in addition to the normal observation in which a color image is displayed on a monitor like viewing by naked eyes. In the auto-fluorescent observation, the diagnosis is performed by using the feature that the auto-fluorescent spectrums outputted from the living-body tissue are varied between the normal mucous membrane and the tumor upon hitting the ultraviolet to blue excitation light to the living-body tissue (refer to, e.g., Japanese Unexamined Patent Application Publication No. 2002-336196). Different colors are assigned to the auto-fluorescent image and the resultant image which are displayed on the monitor together with a reflecting-light image which is reflected and is returned from the living-body tissue, thereby clearly recognizing the lesion.

Since the fluorescent light is weak, an image pick-up device with high sensitivity is necessary for the image pick-up operation. For example, U.S. Pat. Publication No. 5,337,340 suggests one of the image pick-up devices with high sensitivity, comprising a CCD whose amplification rate therein is controlled by inputting a control pulse externally from the image pick-up device. The CCD comprises a CMD (Charge Multiplying Device) arranged therein which can increase the charges by using the ionization. The CMD can be arranged to each pixel, thereby performing the amplification every pixel, and further can be arranged to transfer channels, thereby performing the amplification every transfer line. Advantageously, the variation in amplification rate every pixel in the CMD does not influence and thus the CMD is put into practical use, in which the CMD is arranged to the transfer channel. The amplification rate of the image pick-up device having the CMD in the transfer channel is controlled by changing the amplitude of the control pulse inputted to the CMD (CMD gate pulse). The amplification is-performed in the CCD using the CMD before reading the charges in the CCD. Therefore, there is a merit that the influence of reading noises is suppressed, as compared with the amplification out of the CCD and the image with an excessively high S/N ratio is obtained. The image pick-up operation is possible with high sensitivity and is suitable to the weak light.

SUMMARY OF THE INVENTION

According to the present invention, an image pick-up apparatus comprising: an image pick-up device which picks-up an image of a subject and outputs an image signal; a first-amplitude changing portion which varies an amplitude of the image signal outputted from the image pick-up device; a second-amplitude changing portion which varies an amplitude of the image signal to be outputted; a comparing portion which compares an amplitude of the image signal with a value related to target amplitude; and a control portion which controls the first- and second-amplitude changing portions based on the comparison result of the comparing portion so that an observed image of the subject displayed on display means has a desired brightness, and changes the amplitude of the image signal in order to approximate to the target amplitude, wherein when the control portion controls the operation for increasing the amplitude of the image signal to be inputted to the display means to display the observed image of the subject on the display means more brightly based on the comparison result, the control portion performs the control for varying the amplitude by the first-amplitude changing portion prior to the control for varying the amplitude by the second-amplitude changing portion until the value for varying the amplitude reaches a first value, and performs the control for varying the amplitude of the image signal by the second-amplitude control portion upon controlling the operation for increasing the amplitude of the image signal when the value reaches the first value and when further increasing the amplitude of the image signal, and when the control portion controls the operation for reducing the amplitude of the image signal inputted to the display means to display the observed image of the subject displayed on the display means is more darkly, the control portion performs the operation for controlling the amplitude by the second-amplitude control portion prior to the operation for controlling the amplitude of the image signal by the first amplitude changing portion until the value for varying the amplitude reaches a second value, and performs the operation for varying the amplitude of the image signal by the first-amplitude control portion when further reducing the amplitude of the image signal and when the value reaches the second value.

Further, according to the present invention, an endoscope apparatus comprising: an illuminating-light supply portion which supplies illuminating light for irradiating a subject; an image pick-up device which includes a charge amplifying mechanism for amplifying stored charges; an amplifying portion which amplifies an image signal from the image pick-up device; a light-amount control portion which adjusts the amount of light supplied to the subject by the illuminating-light supply portion; a target setting portion which sets target value of the amplification of charges by the charge amplifying mechanism, of the amplification of the image signal by the amplifying portion, and of light-amount adjustment by the light-amount control portion; a comparing portion which compares the amplitude of the image signal with comparison values based on the target values; and a control portion which controls the charge amplifying mechanism of the image pick-up device, the amplifying portion, and the light-amount control portion based on the comparison result of the comparing portion.

Furthermore, according to the present invention, an endoscope apparatus comprising: an illuminating-light supply portion which supplies illuminating light for irradiating a subject; an image pick-up device for picking-up an image of the subject, the image pick-up device being capable of amplifying stored charges therein; an amplifying circuit which amplifies an image signal from the image pick-up device outside the image pick-up device; and a gain control portion which adjusts an amplification rate of the image signal to amplify the amplification of the image signal so that the image of the subject displayed on the display means has a desired brightness, the gain control portion first performing amplification of the image signal in the image pick-up device when increasing the amplitude of the image signal in the amplifying circuit.

In addition, according to the present invention, an image pick-up apparatus comprising: an image pick-up device which picks-up an image of a subject; a first-amplitude changing portion which changes an amplitude of an image signal from the image pick-up device; a second-amplitude changing portion which changes the amplitude of the image signal from the image pick-up device; a comparing portion which compares the amplitude of the image signal with a set comparison value; and a control portion which changes the amplitude of the image signal so as to be approximate to the set comparison value by controlling the first-amplitude: changing portion or the second-amplitude changing portion in accordance with the comparison result of the comparing portion, the control portion preferentially controlling the amplitude of the image signal by any of the first-amplitude changing portion and the second-amplitude changing portion based on the noise level which is previously assumed to be generated in the amplitude control operation of the image signal by the first-amplitude changing portion and the noise level which is previously assumed to be generated in the amplitude control operation of the image signal by the second-amplitude changing portion.

DESCRIPTION OF THE PREFERRED EMBODIMENTS

An embodiment of the present invention will be described with reference to the drawings. The embodiment of the present invention uses an electronic endoscope apparatus (hereinafter, referred to as an endoscope apparatus) for picking-up an image of an object by using an image pick-up device.

Figure 1:
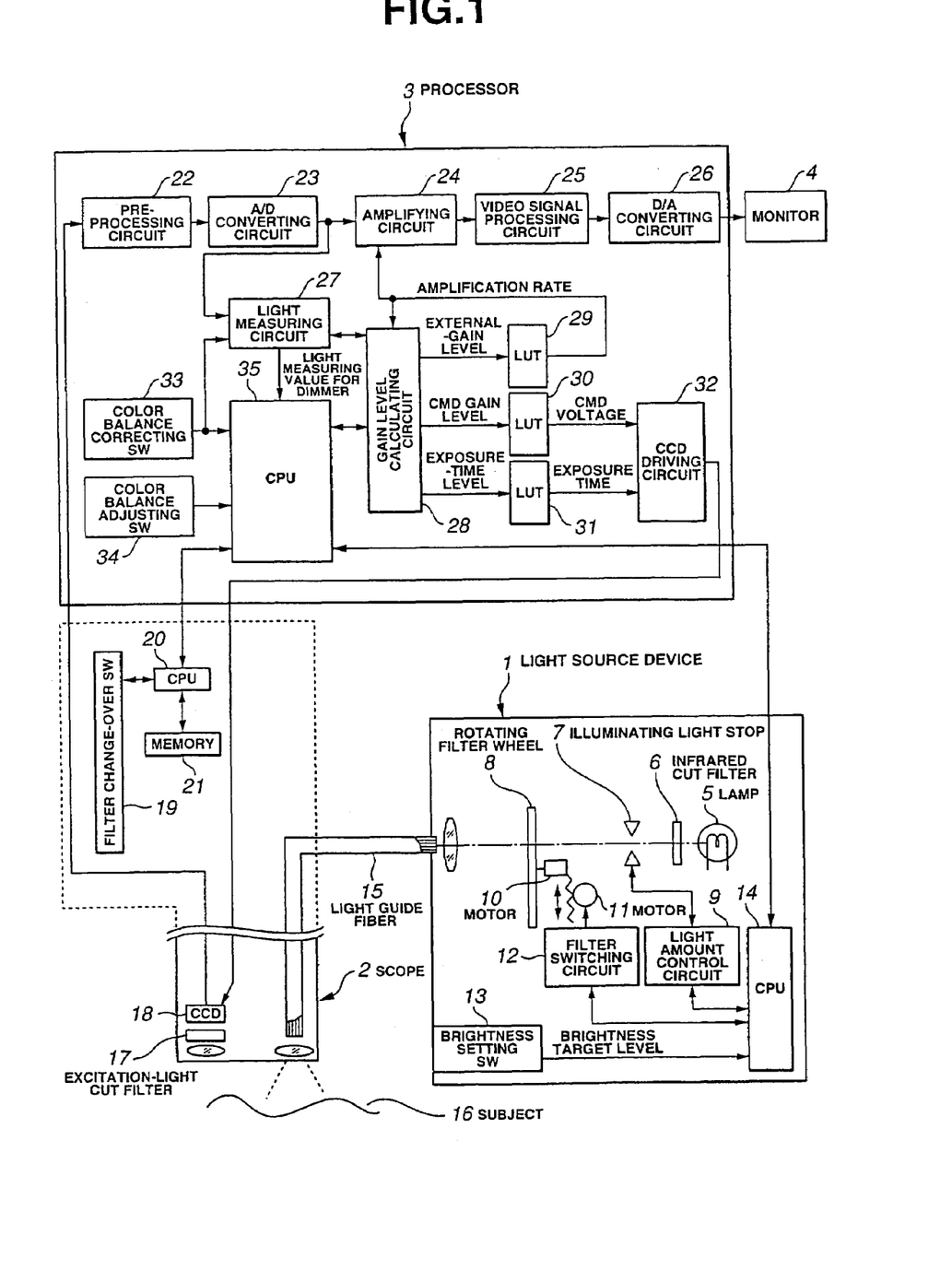
FIG. 1 is a diagram showing the entire structure of an endoscope apparatus according to an embodiment of the present invention.
Figure 2:
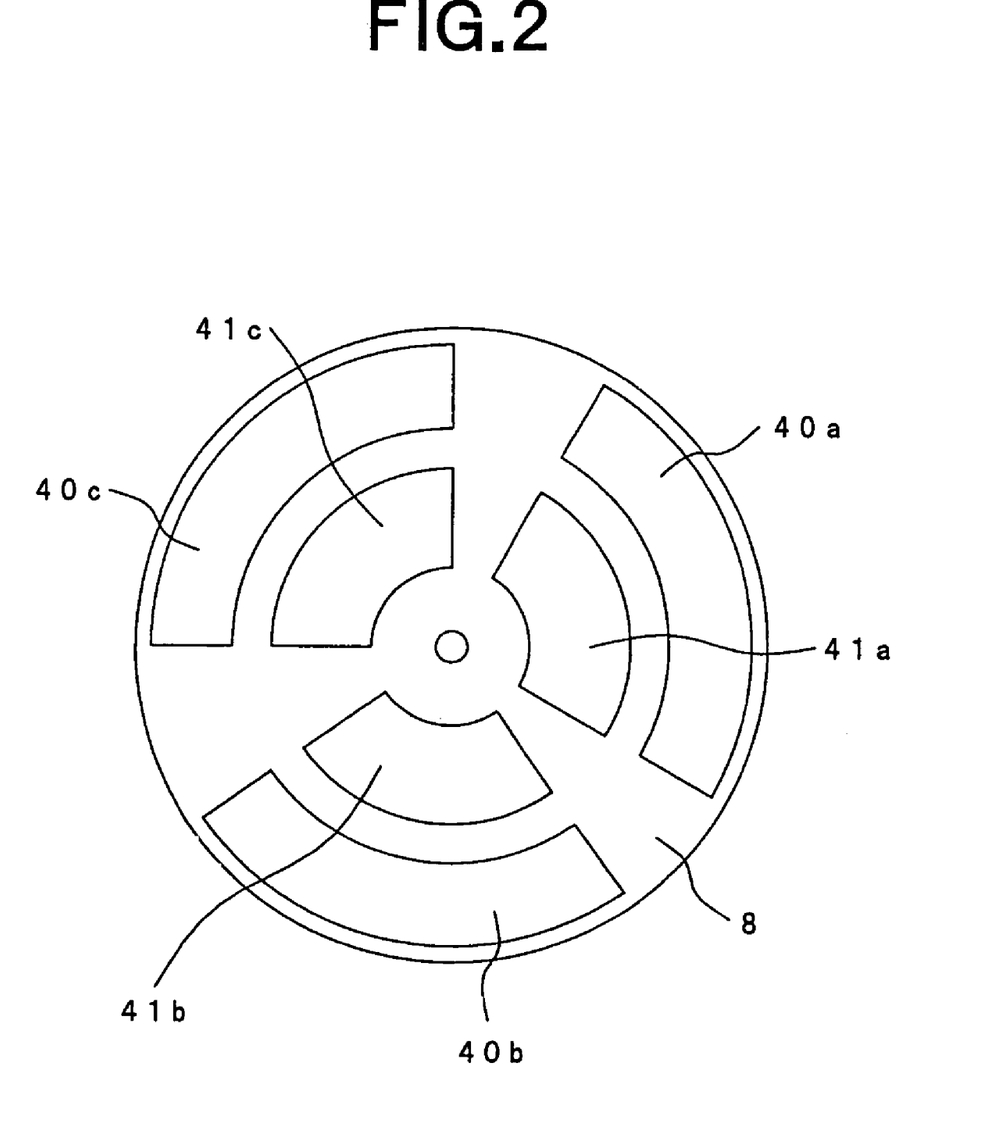
FIG. 2 is an explanatory diagram showing a rotating filter wheel shown in FIG. 1.
Figure 3:
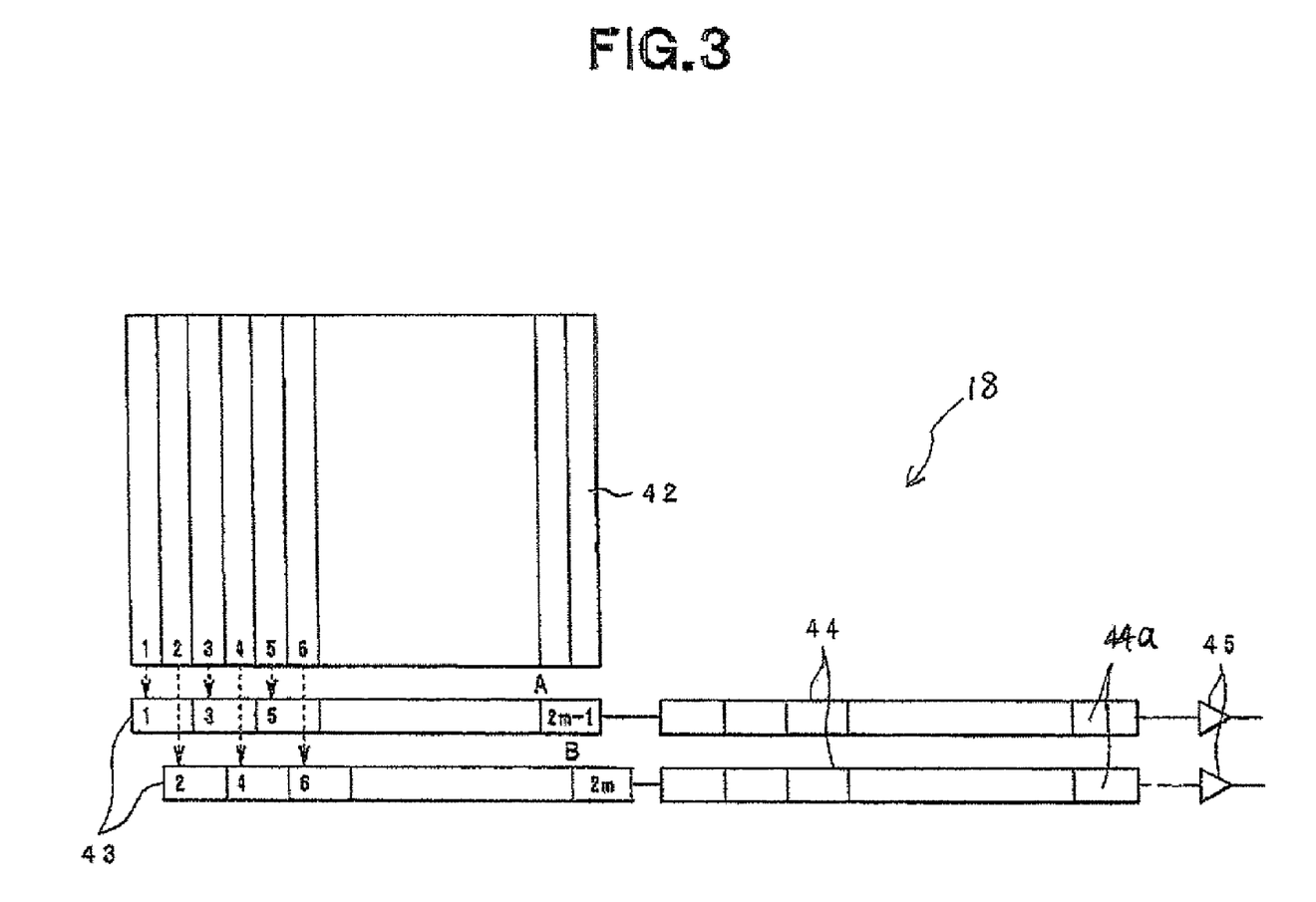
FIG. 3 is an explanatory diagram showing a CCD in FIG. 1.
Figure 4:
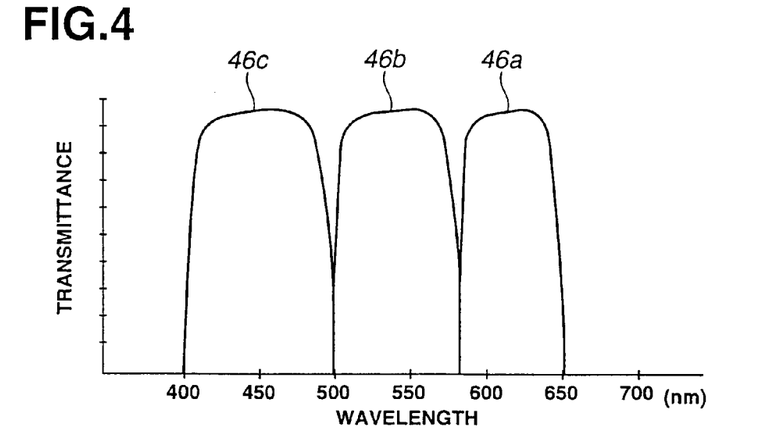
FIG. 4 is a diagram showing the transmittance characteristic of a normal observing filter.
Figure 5:
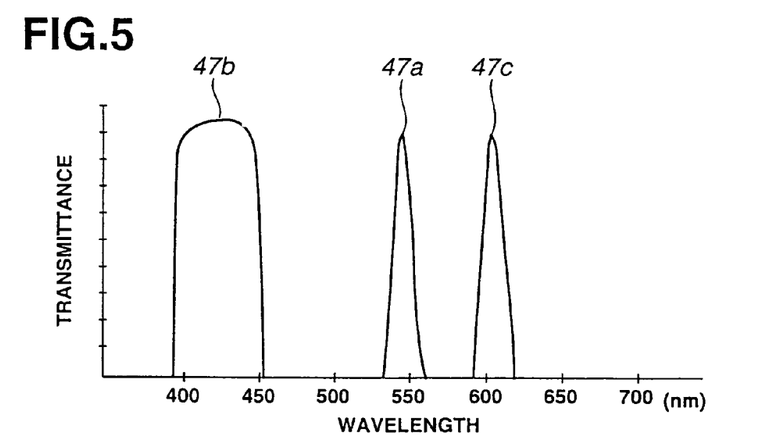
FIG. 5 is a diagram showing the transmittance characteristic of a fluorescent observing filter.
Figure 6:
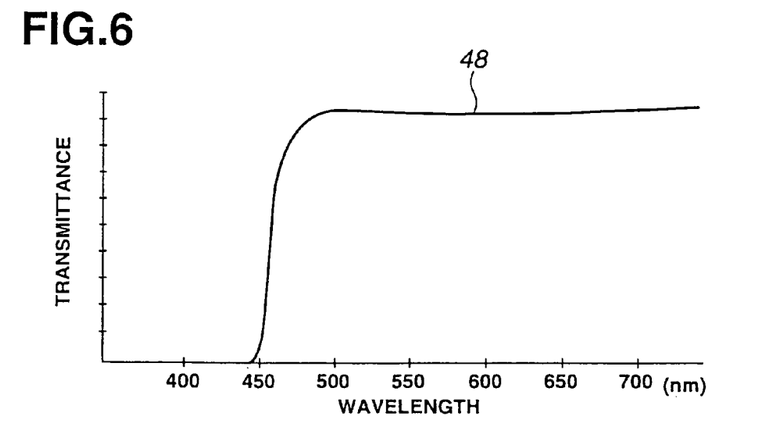
FIG. 6 is a diagram showing the transmittance characteristic of an excitation-light cut filter.
Figure 7:
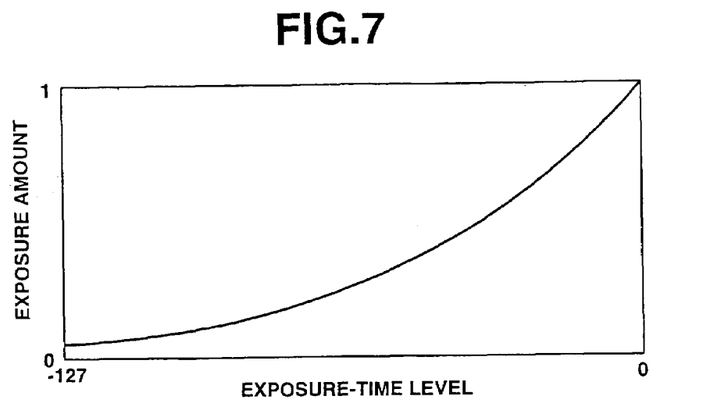
FIG. 7 is an explanatory diagram showing a relationship between the exposure-time level and the exposure amount.
Figure 8:
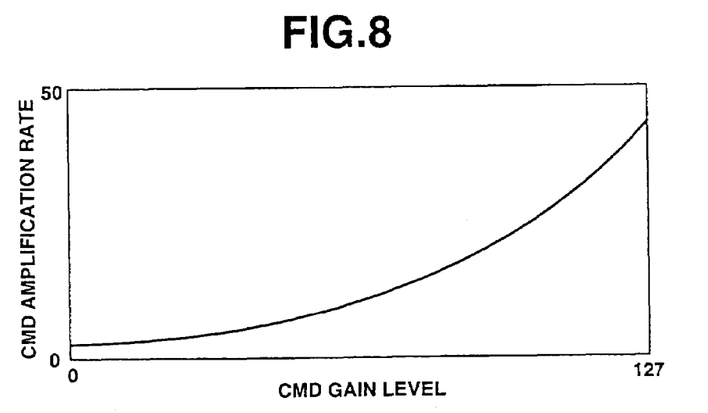
FIG. 8 is an explanatory diagram showing a CMD gain level and a CMD amplification rate.
Figure 9:
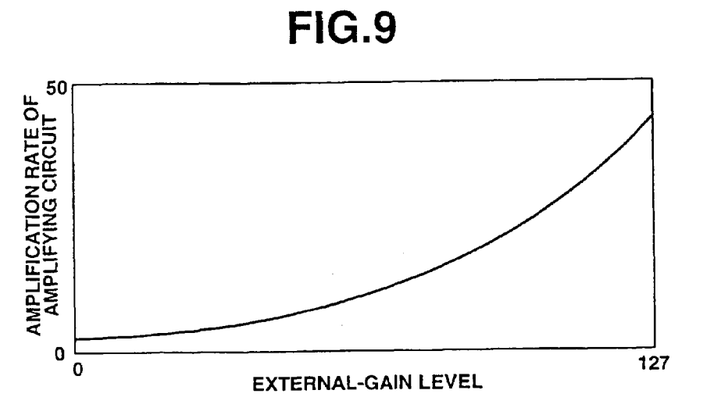
FIG. 9 is an explanatory diagram showing an external-gain level and the amplification rate in an amplifying circuit.
Figure 10:
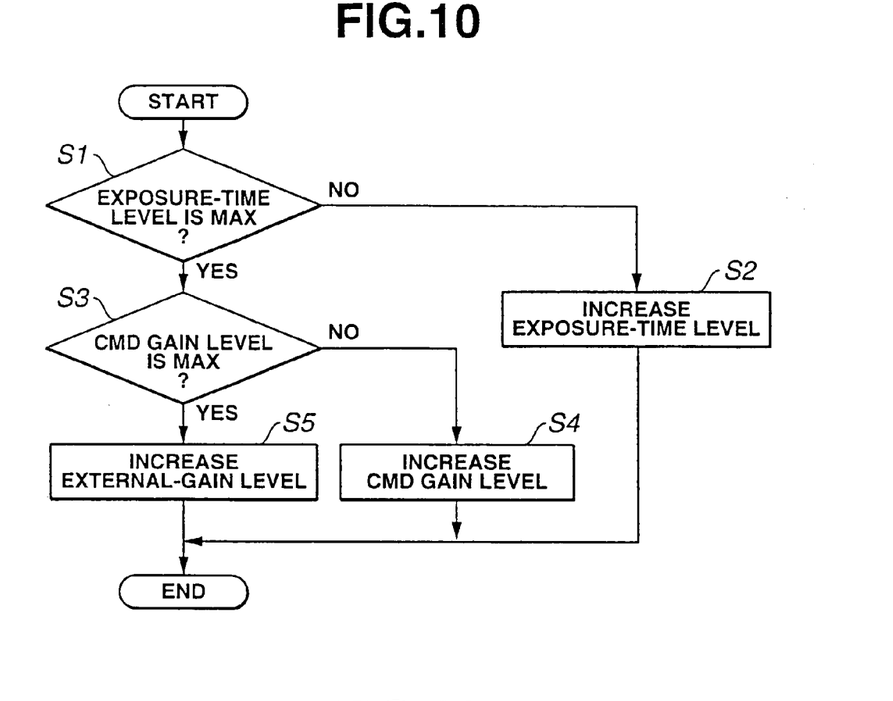
FIG. 10 is a flowchart for increasing the brightness level.
Figure 11:
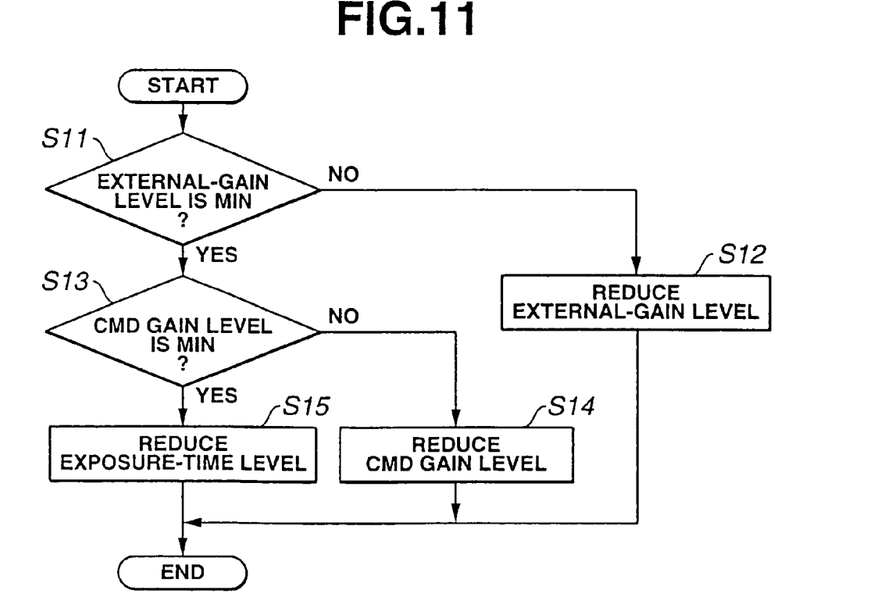
FIG. 11 is a flowchart for reducing the brightness level.
Figure 12:
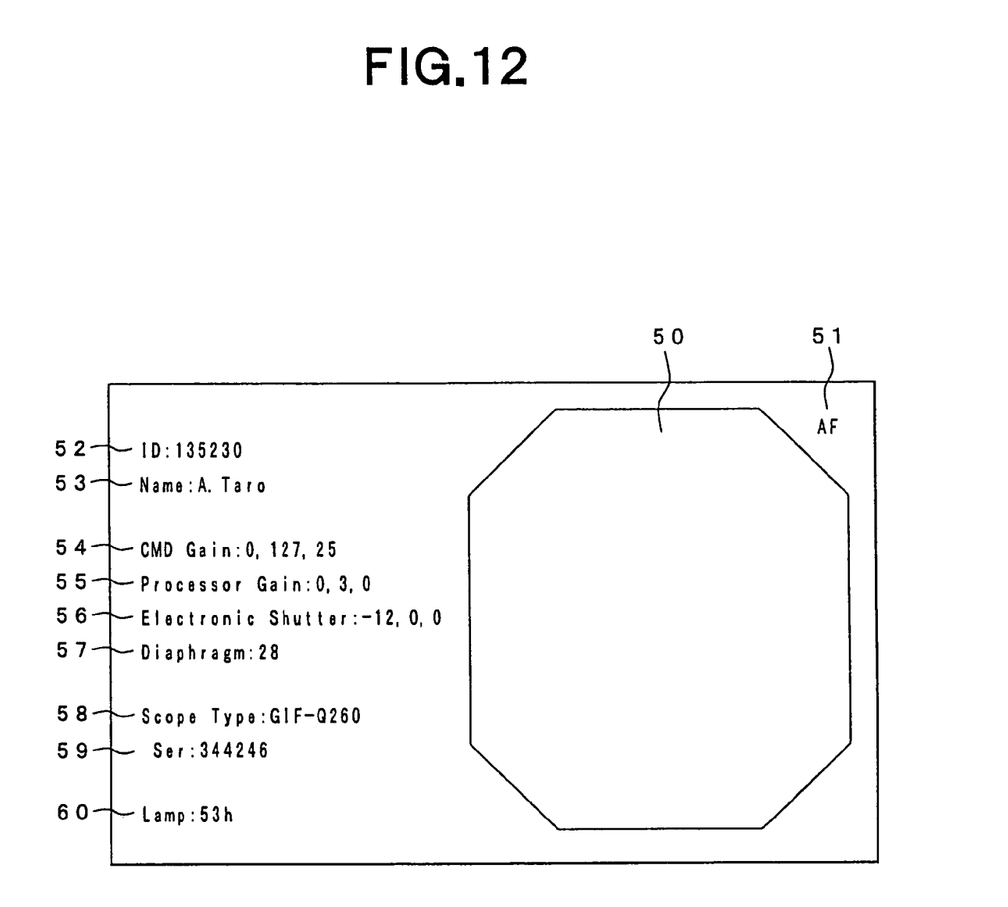
FIG. 12 is an explanatory diagram showing a monitor display screen.

FIG. 1 is a diagram showing the entire structure of an endoscope apparatus according to the embodiment of the present invention. FIG. 2 is an explanatory diagram showing a rotating filter wheel in FIG. 1. FIG. 3 is an explanatory diagram showing a CCD shown in FIG. 1. FIG. 4 is a diagram showing the transmittance characteristic of a normal observing filter. FIG. 5 is a diagram showing the transmittance characteristic of a fluorescent observing filter. FIG. 6 is a diagram showing the transmittance characteristic of an excitation-light cut filter. FIG. 7 is an explanatory diagram showing a relationship between the exposure-time level and the exposure amount. FIG. 8 is an explanatory diagram showing a CMD gain level and a CMD amplification rate. FIG. 9 is an explanatory diagram showing an external-gain level and the amplification rate in an amplifying circuit. FIG. 10 is a flowchart for increasing the brightness level. FIG. 11 is a flowchart for reducing the brightness level. FIG. 12 is an explanatory diagram showing a monitor display screen.

First, the structure according to the embodiment of the present invention will be described.

The entire structure of an endoscope apparatus will be described according to the embodiment with reference to FIG. 1.

According to the embodiment, referring to FIG. 1, an endoscope apparatus comprises: a light source device 1 as illuminating light supply means which emits light for observation; a scope 2 having a CCD 18 as an image pick-up device having the CMD (refer to FIG. 3) and which is inserted in the body cavity; a processor 3 which amplifies an image signal obtained by the CCD 18 and performs the signal processing; and a monitor 4 as a display device for display the image.

The light source device 1 comprises a lamp 5 such as a xenon lamp for radiating the light. On the optical path of the illumination of the lamp 5, the light source device 1 further comprises: an infrared cut filter 6 for limiting the transmitting wavelength; an illuminating light stop 7 which dynamically limits the amount of passing light; and a rotating filter wheel 8 having a plurality of filters through which different wavelengths in the circumferential direction are transmitted.

A light amount control circuit 9 as light amount control means for controlling the amount of passing light is connected to the illuminating light stop 7. A first-amplitude changing portion comprises as a part the light amount control circuit. The rotating filter wheel 8 is mechanically connected to a motor 10 for rotation and a motor 11 for moving the rotating filter wheel 8 vertically in the optical axis. The motor 11 is controlled by a filter switching circuit 12.

At the position of the light source device 1 which is operated by a user, a brightness setting switch 13 as setting means (or target setting portion) is arranged. A central processing unit (CPU) 14 is electrically connected to the brightness setting switch 13, the filter switching circuit 12, and the light amount control circuit 9.

FIG. 2 shows the structure of the rotating filter wheel 8.

Referring to FIG. 2, the rotating filter wheel 8 comprises, at the outer circumference, an R filter 40a, a G filter 40b, and a B filter 40c, through which red (R), green (G), and blue (B) wavelength light is transmitted. Further, the rotating filter wheel 8 comprises, at the inner circumference, a G' filter 41a through which the light within the narrow band of 540 to 560 nm is transmitted, an exciting filter 41b through which the excitation light of 390 to 450 nm is transmitted, and an R' filter 41c through which the light within the narrow band of 600 to 620 nm. A portion except for the arrangement of the filters on the rotating filter wheel 8 comprises a member for shielding the light.

The spectrographic characteristics of the filters at the outer circumference are as shown in FIG. 4. Referring to FIG. 4, reference numeral 46a denotes the characteristic of the R filter 40a, reference numeral 46b denotes the characteristic of the G filter 40b, and reference numeral 46c denotes the characteristic of the B filter 40c. The spectrographic characteristics of the filters at the inner circumference are as shown in FIG. 5. Referring to FIG. 5, reference numeral 47a denotes the characteristic of the G' filter 41a, reference numeral 47b denotes the characteristic of the exciting filter 41b, and reference numeral 47c denotes the characteristic of the R' filter 41c.

Referring to FIG. 1, the scope 2 comprises: a light guide fiber 15 which transmits the illuminating light; and a long and thin inserting portion which can be inserted in the living body. The inserting portion comprises, at the distal end: an excitation-light cut filter 17 which removes the excitation light; an image pick-up device (CCD) 18 with the CMD for picking-up the light from an object 16; a filter change-over switch 19 which instructs the switching operation of the filters; a CPU 20; and a memory 21 which stores information on the scope. The CMD functions as a second-amplitude changing portion.

The excitation-light cut filter 17 inserted at the distal end of the scope 2 has the transmittance characteristics shown in FIG. 6. The excitation-light cut filter 17 has a function for shielding the light with the wavelength of 460 nm or less and for removing the excitation light.

FIG. 3 shows the structure of the CCD 18.

Referring to FIG. 3, the CCD 18 comprises: a light receiving area 42 having a plurality of photoelectrically converting devices (not shown); a horizontal transfer channel 43 comprising a horizontal register for horizontally transferring the charges stored in the light receiving area 42; a transfer channel 44 with the CMD (including a CMD 44a) which is connected to the latter part of the horizontal transfer channel 43 and which transfers the charges from the horizontal transfer channel 43 to a charge detecting portion 45 such as a CDS portion. The charges are read independently in an odd line and an even line via two A and B channels. As mentioned above, in the CCD 18, the CMD 44a is arranged to the horizontal register and can amplify each horizontal transfer line, and the variable amplification is possible by an external control-pulse.

Referring to FIG. 1, the processor 3 comprises: a pre-processing circuit 22 for performing the processing of the CDS (Correlative Double Sampling); an A/D converting circuit 23 which converts an analog signal into a digital signal; an amplifying circuit 24 as amplifying means for varying the amplification rate or a third-amplitude changing portion; a video signal processing circuit 25; and a D/A converting circuit 26 which converts the digital signal into the analog signal so as to send an image signal in the order thereof. Further, the processor 3 comprises: a light measuring circuit 27 which receives the signal after the A/D conversion; a gain level calculating circuit 28 as gain control means or control means comprising a microprocessor; look-up tables (hereinafter, referred to as LUTS) 29, 30, and 31; a CCD driving circuit 32 which functions as exposure amount control means (exposure amount control portion), exposure time control means, and CMD control means; a color balance correcting switch 33; a color balance adjusting switch 34; and a CPU 35 having a comparing portion. The main electric connection is as shown in FIG. 1. The color balance correcting switch 33 and the color balance adjusting switch 34 are arranged at the position which is easily operated by the user.

Next, the operation according to the embodiment of the present invention will be described.

Hereinafter, the operation upon the fluorescent observation (specific-light observing mode) will mainly be described.

The light for illuminating the object 16 is irradiated from the lamp 5 in the light source device 1. The light irradiated from the lamp 5 passes through the infrared cut filter 6, the illuminating light stop 7, and the rotating filter wheel 8, and is further incident on the light guide fiber 15 of the scope 2. The infrared cut filter 6 cuts-off the infrared light, and shields the unnecessary heat and light which are irradiated to the filters on the rotating filter wheel 8. The light amount control circuit (exposure amount control portion) 9 controls the illuminating light stop 7 so as to output the video signal with predetermined brightness to the monitor 4. The brightness as the target can be changed at some steps by operating the brightness setting switch 13 by the user. The target level of the brightness (target amplitude of the image signal) set by the brightness setting switch 13 is used by the gain level calculating circuit 28 as well as by the light amount control circuit 9. As mentioned above, the single brightness setting switch 13 sets the target levels of both the light amount control means and the gain control means. Therefore, the user easily adjusts the brightness of the image displayed on the monitor 4 as the display device.

In the fluorescent observation, the rotating filter wheel 8 is moved in the vertical direction of the optical axis together with the motor 11 by rotationally driving a pinion (not shown) screwed to a rack attached to the motor 10 by the motor 11 in accordance with the signal from the filter switching circuit 12 based on the operation of the filter change-over switch 19. Thus, an inner-circumferential filter 41 is inserted on the optical path. Upon inserting the inner-circumferential filter 41, the light with the wavelengths of 540 to 560 nm, 390 to 450 nm, and 600 to 620 nm is sequentially outputted from the light source device 1. The light of 390 to 450 nm is the excitation light for exciting the auto-fluorescent from the living-body tissue. As mentioned above, the filter change-over switch 19 is turned to the side of the fluorescent observing mode and thus the light source device 1 sequentially supplies, to the light guide fiber 15, the illuminating light in the fluorescent observing mode, namely, the transmitting light of the filters 41a, 41b, and 41c (refer to FIG. 2). Further, the processor 3 enters the state for the signal processing in accordance with the fluorescent observing mode. In the normal observation, an outer-circumferential filter 40 is inserted on the optical axis based on the operation of the filter change-over switch 19. The motor 10 rotationally drives the outer-circumferential filter 40 at a predetermined speed, thereby sequentially inserting the R filter 40a, the G filter 40b, and the B filter 40c on the optical path. Then, the red (R), green (G), and blue (B) light is transmitted. That is, the filter change-over switch 19 is turned to the side of the normal observing mode and then the light source device 1 sequentially supplies, to the light guide fiber 15, the illuminating light in the normal observing mode, namely, the transmitting light R, G, and B through the R filter 40a, the G filter 40b, and the B filter 40c (refer to FIG. 2). Further, the processor 3 enters the state for the signal processing in accordance with the normal observing mode.

The CPU 14 sends the target level of the brightness set by the brightness setting switch 13 to the gain level calculating circuit 28, via the light amount control circuit 9 and the CPU 35 of the processor 3.

The light amount control circuit 9 compares the target level of the brightness set by the brightness setting switch 13 with measuring light for dimmer which is calculated by the light measuring circuit 27 in the processor 3 and sent via the CPU 35 in the processor 3 and the CPU 14 in the light source device 1, and generates a control voltage. Further, the light amount control circuit 9 controls the illuminating light stop 7 so that the brightness of the video signal is close to the target level. Therefore, the exposure amount can be also controlled by controlling the illuminating light stop and controlling the light amount. A control voltage for controlling the illuminating light stop 7 is sent from the light amount control circuit 9 to the CPU 35 via the CPU 14. The control voltage outputted from the light amount control circuit 9 has a value corresponding to the opening degree of the stop, and becomes a key for knowing the level of the amount of illuminating light.

The light incident on the light guide fiber 15 of the scope 2 is irradiated to the object 16 such as the gastrointestinal tract from the distal end of the scope. The light scattered, reflected, and radiated by the object 16 is formed onto the CCD 18 at the distal end of the scope, and is picked-up. The excitation-light cut filter 17 is inserted in front of the CCD 18, having a function for shielding (cutting) the excitation light of 390 to 450 nm and extracting the fluorescent light.

The CCD 18 is driven by the CCD driving circuit 32 in the processor 3 synchronously with the rotation for the rotating filter wheel 8. Then, the signals corresponding to the illuminating light transmitted through the respective filters at the inner circumference of the rotating filter wheel 8 such as the G' filter 41*a*, the exciting filter 41*b* and the R' filter 41*c* are sequentially outputted to the processor 3. The CMD gate pulse is inputted to the CMD 44*a* from the CCD driving circuit 32, thus, secondary electrons due to the impact ionization are generated in the CCD 18, and the signal charges (stored charges) are amplified. Here, the amplification rate is controlled by the amplitude of the CMD gate pulse. The CCD driving circuit 32 inputs a charge sweeping pulse if necessary, and adjusts the exposure time. Thus, the exposure amount of an image pick-up device is adjusted.

According to the embodiment, the CMD 44*a* with the low deterioration of the S/N ratio is preferentially used for the amplification by arranging the gain control means including a gain level calculating circuit 28 for controlling the amplification of the amplifying circuit 24, which is located in and out of the CCD 18, and the amplification of the CMD 44*a* in the scope 2. Further, when an image of the dark object is picked-up, the amplification is performed in/out of the CCD 18, so that the image with the sufficient brightness is obtained. When an image of the relatively-bright object is picked-up, the amplification is performed only by the CCD 18, so that the image with the high S/N ratio is obtained.

The image signal inputted to the processor 3 is first inputted to the pre-processing circuit 22. The pre-processing circuit 22 extracts the image signal by the CDS (Correlative Double Sampling) or the like. The signal outputted from the pre-processing circuit 22 is converted into a digital signal from the analog signal by the A/D converting circuit 23. The signal outputted from the A/D converting circuit 23 is inputted to the amplifying circuit 24. The amplifying circuit 24 amplifies the signal by the amplification rate instructed from the LUT 29 every irradiating wavelength. The video signal processing circuit 25 emphasizes the emphasis of the image color or contour and corrects the gamma characteristics, the D/A converting circuit 26 converts the corrected signal into the analog signal, and the monitor 4 displays it thereon. In the fluorescent observation, the monitor 4 displays, as the R-, G-, and B-signals, the reflecting light of the green within the narrow band (G' signal), fluorescent signal (F signal), and reflecting signal (R' signal) of red within the narrow band are displayed. In the normal observation, the monitor 4 displays, as the R-, G-, and B-signals, the components of the red, green, and blue reflecting light.

The light measuring circuit 27 calculates the screen average (light-measuring value) of the brightness of the video signal based on the fluorescent component in the fluorescent observation and the luminance signal in the normal observation. Further, upon pressing the color balance correcting switch 33, the light measuring circuit 27 calculates the screen average (light-measuring value) of the image signal every irradiating wavelength. That is, the light measuring circuit 27 has a function as a sampling circuit for correcting the color balance. The light-measuring light for dimmer, which is outputted from the light measuring circuit 27 and is sent to the light amount control circuit 9 via the CPU 35 in the processor 3 and the CPU 14 in the light source device 1, is obtained by dividing the screen average of brightness by the CMD amplification rate upon obtaining the image, namely, is the screen average which is obtained when the CMD 44*a* does not perform the amplification. The dividing value is outputted, thereby outputting the screen average when the CMD 44*a* does not, perform the amplification. Therefore, the amount of illuminating light is kept to be proper. As mentioned above, the light-measuring value for dimmer from the light measuring circuit 27 to the light amount control circuit 9 is the screen average of the image signal every irradiating wavelength to be obtained when the CMD 44*a* does not perform the amplification. Therefore, when the amplification rate of the CMD 44*a* is high and the scope 2 moves in the close direction and the screen is bright, it is prevented that the amount of illuminating light is decreased by stopping the light by the illuminating light stop 7 irrespective of the brightness adjusting range due to the reduction in amplification rate of the CMD 44*a*. In this case, if the illuminating light stop 7 reduces the amount of illuminating light, the brightness of the image is kept to be proper by adjusting the amplification rate of the CMD 44*a*. However, the image with the low noises is obtained by compensating for the insufficient brightness by the opening of the illuminating light stop 7 and the amplification of the CMD 44*a*. As mentioned above, the illuminating light stop 7 acts only when the object 16 is close to the scope 2 and the brightness is high by the amplification rate as one of the CMD 44*a* or the amplifying circuit 24.

Upon correcting the color variation due to the individual difference of the scope 2 or the light source device 1, the user presses the color balance correcting switch 33 while picking-up the image of the object 16 as the color reference, thereby setting the maximum exposure-time for the entire irradiating wavelength and one time of the CMD gain for the entire irradiating wavelength from the CPU 35 via the gain level calculating circuit 28. The gain of the G' signal and R' signal for the F signal is calculated in the fluorescent observation based on the brightness of the image for the irradiating wavelengths calculated by the light measuring circuit 27, and the calculated gain is sent to the gain level calculating circuit 28. The maximum exposure time means that the exposure-time level is set to be the same exposure amount without sweeping the charges in the CCD 18. The characteristics of the filters shown in FIG. 5 are designed in consideration of the individual variation so that the gain of the G' signal and R' signal is 1 or less.

The gain level calculating circuit 28 calculates the exposure-time levels based on the gain of the G' signal and R' signal sent from the CPU 35 so that the F signal, G' signal, and R' signal are the same, and outputs the calculated level to the LUT 31. The LUT 31 outputs the exposure time so that the exposure time is increased to 1.03 times every time increasing the exposure-time level.

FIG. 7 shows a relationship between the exposure amount and the exposure-time level inputted to the LUT 31. When the input level is 0, the exposure time is maximum and the maximum exposure amount is 1. Here, the necessary gain is designated by reference symbol $\alpha 1$. Then, the exposure-time level is expressed by $\log(\alpha 1)/\log(1.03)$. The luminous fluxes crossing the rotating filter wheel 8 have an area and therefore the exposure time and the exposure amount are not completely proportional. However, the LUT 31 stores the value in consideration of the non-linear component.

In the observation, each time for one rotation of the rotating filter wheel 8, the gain level calculating circuit 28 compares the value obtained by multiplying the amplification rate of the amplifying circuit 24 to the brightness of the image calculated by the light measuring circuit 27 with the target level of brightness set by the brightness setting switch 13, and determines the external-gain level, CMD gain level, and the exposure time level. When the obtained value is lower than the target level, the brightness levels of the F signal, G' signal, and R' signal are increased by one level. When the obtained value is higher than the target level, the brightness levels are reduced by one level. The gain level calculating circuit 28 stores in the memory, every observing mode, the exposure time level, the CMD gain level, and the external gain level of the F signal, G' signal, and the R' signal.

FIG. 10 shows a flowchart for increasing the brightness level (amplitude of the image signal) of the signal by one level. First, it is checked whether or not the exposure-time level (or exposure-amount level) of the current G' signal is maximum (whether reaches a first value) (step S1). If NO in step S1, the exposure-time level is increased by one level (step S2) and the processing ends. If YES in step S1, it is checked whether or not the CMD gain level of the current F signal is maximum (whether or not the amplification of stored charges reaches a third value) (step S3). If NO in step S3, the CMD gain level is increased by one level (step S4) and the processing ends. When the CMD gain level is maximum, the external-gain level of the current G signal is increased by one level (step S5). The same operation increases the brightness levels of the F signal and G' signal.

Since the exposure amount is increased without the deterioration of the S/N ratio prior to the electric amplification, the image with the high S/N ratio is obtained. Also, since the set upper limit value (maximum value) is provided for the gain of the CMD amplification, the electric safety of the scope is easily kept because the high voltage is not applied to the CMD. Further, the unnecessary discharge of electromagnetic waves is suppressed.

FIG. 11 shows a flowchart for reducing the brightness level by one level. In this case, in steps S11 to S15, on the contrary to the increase in brightness level, in the level reducing order, the external-gain level, the CMD gain level, and the exposure-time level are reduced by searching the reduction-possible level.

That is, it is checked to see if the external-gain level of the current G' signal is minimum (if the amplification of the image signal reaches a fourth value) (step S11). If NO in step S11, the external-gain level is reduced by one level (step S12) and the processing ends. If YES in step S11, it is checked to see if the CMD gain level of the current F signal is minimum (if the amplification of stored charges reaches a second value) (step S13). If NO in step S13, the CMD gain level is reduced by one level (step S14) and the processing ends. If the CMD gain level is minimum, the exposure-time level of the current G signal is reduced by one level (step S15). The same operation for the F signal and G' signal reduces the brightness level.

When the external-gain levels of the F signal and the CMD gain level are zero and the video signal is brighter than the target level, the brightness levels (gain levels of the F signal, G' signal, and the R' signal) are not reduced to the level of the current video signal or less. In this case, the light amount control circuit 9 acts and therefore the brightness level is adjusted to the proper one. When any of the external-gain levels of the F signal, the G' signal, and the R' signal is maximum and the video signal is darker than the target level, the brightness level is kept so as to prevent the deterioration of the image tone without the increase in brightness level.

The LUT 29 outputs the amplification rate shown in FIG. 9 for the inputted external-gain level. That is, when the external-gain level is 0, the amplification rate is one. Further, each time when the external-gain level increases by one, the amplification rate of the amplifying circuit 24 increases by 1.03 times.

The LUT 30 outputs the CMD voltage so as to obtain the CMD amplification rate as shown in FIG. 8 for the inputted CMD gain level. That is, when the CMD gain level is zero, the CMD amplification rate is one time. Each time when the CMD gain level increases by one, the amplification rate of the CMD 44a increases by 1.03 times.

In the entire LUT 29, LUT 30, and LUT 31, the change of the input level 1 corresponds to the 1.03-time change of the signal. Therefore, the tone is easily kept upon individually controlling the F signal, G' signal, and R' signal. According to the embodiment, for the F signal, G' signal, and R' signal, the exposure time without the increase in noises, the CMD amplification with the relatively low increase in noises, and the external amplification which is easily influenced from the noises are individually increased. Under the condition that the noises are reduced at the highest level for any signals, the image can be obtained.

The CCD driving circuit 32 sends, to the CCD 18, the CMD gate pulse of the CMD voltage instructed from the LUT 30 every irradiating wavelength, and the amplifying mechanism of the CMD 44 acts. Further, the CCD driving circuit 32 controls the exposure amount by sending a charge sweeping-out pulse to the CCD 18 so as to obtain the exposure time instructed by the LUT 31 every irradiating wavelength. As mentioned above, the CMD voltage and the charge sweeping timing are adjusted every irradiating wavelength.

When the user wants to perform the observation with his/her desired color, the color balance adjusting switch 34 instructs the increase/reduction of the gain of the G' signal or R' signal. The color balance adjusting switch 34 sends an instructing signal to the gain level calculating circuit 28 via the CPU 35, and the gain level calculating circuit 28 increases/reduces the brightness level of the G' signal or R' signal in the order similar to that shown in FIG. 10 or 11.

When the user adjusts the brightness of the image outputted to the monitor 4, the brightness setting switch 13 of the light source device 1 is pressed. Then, the brightness setting switch 13 sends the new brightness-target level to the light amount control circuit 9 and the gain level calculating circuit 28, and the control operation is performed in the circuits. Thus, the image can be observed with the user's desired brightness on the monitor 4.

The operator presses the filter change-over switch 19, then, the CPU 20 recognizes the pressing operation, and the motor 11 is driven via the CPU 35 of the processor 3, the CPU 14 of the light source device 1, and the filter switching circuit 12. Then, the outer-peripheral filters and the inner-peripheral filters of the rotating filter wheel 8 are switched and further the observing modes (normal observation and fluorescent (specific-light) observation) are switched. Simultaneously, the various settings of the gain level and the like in the processor 3 are switched between the normal observation and the fluorescent observation.

Referring to FIG. 12, on the monitor 4, a superimposing circuit (not shown) superimposes and displays an observing mode 51, a CMD gain level (CMD Gain) 54, an external-gain level (Processor Gain) 55, an exposure-time level. (Electronic Shutter) 56, a light-source stop voltage (Diaphragm) 57, a scope type 58, a Ser. No. 59 of the scope, and a lamp using time (Lamp) 60 as well as an observing screen 50, a patient ID 52, and a patient Name 53. Three values of the CMD gain level, the external-gain level, and the exposure-time level are shown to express the value every irradiating wavelength. The display operation of the value enables the operating state of the devices to be grasped and provides useful information for parameter setting in the evaluation of the recorded image in the back order or in the image processing.

As described above, according to the embodiment, when the brightness of the image is not sufficient, the prior use of the means with the low influence to the S/N ratio is preferable, that is, (1) increase in amount of illuminating light (exposure amount), (2) increase in exposure time (exposure amount), (3) increase in CMD amplification rate, and (4) increase in amplification rate of the amplifying circuit 24. In this case, the image is always observed with the optimum S/N ratio. On the contrary, when the image is highly bright, the prior use of the means with the high influence to the S/N ratio is preferable, that is, (1) reduction in amplification rate of the amplifying circuit, (2) reduction in CMD amplification rate, (3) reduction in exposure time, and (4) reduction in amount of illuminating light.

According to the embodiment, the fluorescent light in the visible area is applied to the endoscope apparatus for observation. Further, as disclosed in Japanese Unexamined Patent Application Publication No. 2002-95635, the fluorescent light can advantageously be used for the reflecting-light observation using the three wavelengths within the narrow bands or for the observation using the infrared reflecting light and the fluorescent light.

The gain level calculating circuit 28 is not limited to the gain level calculating circuit using the microprocessor and may be the gain level calculating circuit using the look-up table. Or, the CPU 35 may have the gain level calculating circuit, thereby inputting the external-gain level, CMD gain level, and exposure-time level to the LUTs 29 to 31 with a CPU bus.

Further, the brightness level may be increased/reduced every several levels for each rotation of the rotating filter wheel 8, thereby properly converging the brightness level to the best brightness one. Alternatively, the brightness level may adaptively be increased/reduced in accordance with the difference between the target level and the actual signal brightness level.

When the amplification rate of the CMD 44a and the amplification rate of the amplifying circuit 24 are independently controlled by individual gain control means, the common brightness-target level set by the brightness setting switch 13 is used and thus, advantageously, the brightness control is easy.

The amplification of the processor 3 is not limited to that using the digital operation and the signal may be amplified before the A/D conversion so as to prevent the calculation error caused by the digital amplification.

According to the embodiment, the scope 2 having the CMD is described. Further, a fact indicating whether or not the CMD is provided is stored in the memory of the scope 2. When the scope without the CMD is connected, the only the CMD gain level is fixed to zero so as to correspond to the scope without the CMD.

Further, in the scope which does not control the exposure time, a fact indicating whether or not the exposure time is controlled is stored in the memory of the scope 2. When the scope which does not control the exposure time is connected, only the exposure-time level is fixed to zero. Other portions are controlled similarly to the embodiment, thereby corresponding to the scope which does not control the exposure time.

The observation of the normal image does not need the high amplification rate. Therefore, the external-gain level and the CMD gain level may be fixed to zero in the normal observation.

Information on the individual variation on the CMD amplification rate is inputted to the memory of the scope 2, it is used as correcting data in the control of the CMD voltage, and the accurate color reproduction may be performed.

Next, the advantages of the embodiment of the present invention will be described.

The gain control means for controlling the amplification of the CMD and the external amplifying circuit is arranged and the amplification is performed by preferentially using the CMD with the low deterioration of the S/N ratio. Therefore, upon picking-up the image of the dark object, the image with the sufficient brightness is obtained. Upon picking-up the image of the object with the relatively high brightness, the image with the high S/N ratio is obtained.

Prior to the electric amplification, the exposure amount is increased without the deterioration of the S/N ratio. Therefore, the image with the high S/N ratio is obtained.

The single brightness-setting switch sets both the target levels of the light amount control circuit and the control means. Therefore, the user can easily adjust the brightness of the image displayed on the display device.

Since the CMD amplifying gain has an upper limit value, the CMD does not need the high voltage. Therefore, the electric safety of the scope is easily kept and the unnecessary electromagnetic discharge is suppressed.

As mentioned above according to the embodiment of the present invention, the endoscope apparatus in which the image pick-up device picks-up the image of the object is used for the improvement of the S/N ratio. Further, the image pick-up device such as a video camera can be used for the improvement of the S/N ratio.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An image pick-up apparatus comprising:
   an image pick-up device which picks-up an image of a subject and outputs an image signal;
   a first-amplitude changing portion which varies an amplitude of the image signal outputted from the image pick-up device by varying an exposure amount of the image pick-up device;
   a second-amplitude changing portion which varies an amplitude of the image signal to be outputted by the image pick-up device;
   a comparing portion which compares an amplitude of the image signal with a value related to target amplitude; and
   a control portion which controls the first- and second-amplitude changing portions based on the comparison result of the comparing portion so that an observed image of the subject displayed on display means has a desired brightness, and changes the amplitude of the image signal in order to approximate to the target amplitude, wherein when the control portion controls the operation for increasing the amplitude of the image signal to be inputted to the display means to increase the brightness of the observed image of the subject on the display means based on the comparison result, the control portion performs the control for varying the amplitude by the first-amplitude changing portion prior to the control for varying the amplitude by the second-amplitude changing portion until the value for varying the amplitude reaches a first value, and performs the control for varying the amplitude of the image signal by the second-amplitude control portion upon controlling the operation for increasing the amplitude of the image signal when the value reaches the first value and when further increasing the amplitude of the image signal, and when the control portion controls the operation for reducing the amplitude of the image signal inputted to the display means to decrease the brightness of the observed image of the subject displayed on the display means, the control portion performs the operation for controlling the amplitude by the second-amplitude control portion prior to the operation for controlling the amplitude of the image signal by the first amplitude changing portion until the value for varying the amplitude reaches a second value, and performs the operation for varying the amplitude of the image signal by the first-amplitude control portion when farther reducing the amplitude of the image signal and when the value reaches the second value.

2. An image pick-up apparatus according to claim 1, wherein the image pick-up device has the second-amplitude changing portion, and the second value is a lower limit of an amplification rate of stored charges, and wherein the second-amplitude changing portion changes the amplitude of the image signal to be outputted by changing the amplification rate of stored charges, until the amplification rate reaches the second value when performing the operation for reducing the amplitude of the image signal inputted to the display means so as to reduce the brightness of the observed image of the subject displayed on the display means.

3. An image pick-up apparatus according to claim 2, wherein the first value is the upper limit of the value for varying the exposure amount of the image pick-up device, and the first-amplitude changing portion changes the amplitude of the image signal by changing the exposure amount of the image pick-up device until the value for varying the exposure amount reaches the first value.

4. An image pick-up apparatus according to claim 2, wherein the first-amplitude changing portion comprises an exposure-time adjusting portion which adjusts the exposure amount by adjusting an exposure time of the image pick-up device.

5. An image pick-up apparatus according to claim 4, wherein the first-amplitude changing portion comprises a light-amount adjusting portion which adjusts the amount of illumination light on the subject.

6. An image pick-up apparatus according to claim 3, further comprising:
a third-amplitude changing portion which is externally arranged to the image pick-up device and varies an amplitude of the image signal to be outputted by changing the amplification rate,
wherein the second-amplitude changing portion changes the amplitude of the image signal until the amplification rate reaches a third value provided as the upper limit when performing the operation for increasing the amplitude of the image signal inputted to the display means so as to increase the brightness of the observed image of the subject displayed on the display means, and the control portion controls the operation for changing the amplitude by the third-amplitude changing portion when the value for varying the exposure amount of the image pick-up device reaches the first value and the amplification rate controlled by the third-amplitude changing portion reaches the third value, upon performing the operation for increasing the amplitude of the image signal inputted to the display means so as to increase the brightness of the observed image of the subject displayed on the display means.

7. An image pick-up apparatus according to claim 6, further comprising:
a third-amplitude changing portion which is externally arranged to the image pick-up device and varies the amplitude of the image signal outputted by changing the amplification rate,
wherein the third-amplitude changing portion changes the amplitude of the image signal until the amplification rate reaches a fourth value provided as the lower limit when performing the operation for reducing the amplitude of the image signal inputted to the display means so as to reduce the brightness of the observed image of the subject displayed on the display means, and the control portion controls the operation for changing the amplitude by the first-amplitude changing portion when the amplification rate of stored charges controlled by the second-amplitude changing portion reaches the second value and when the amplification rate of the image signal controlled by the third-amplification changing portion reaches the fourth value, upon performing the operation for reducing the amplitude of the image signal inputted to the display means so as to reduce the brightness of the observed image of the subject displayed on the display means.

8. An image pick-up apparatus according to claim 5, further comprising:
a setting portion which sets target value for changing the amplitude of the image signal, the first-amplitude changing portion and the second-amplitude changing portion performing the amplitude control operation based on the target value.

9. An image pick-up apparatus according to claim 7, further comprising:
a setting portion which sets target value for changing the amplitude of the image signal, the first-amplitude changing portion and the second-amplitude changing portion performing the amplitude control operation based on the target value.

10. An image pick-up apparatus according to claim 1, wherein a normal observing mode for obtaining the observed image of the subject by normal light and a specific-light observing mode for obtaining the observed image of the subject by specific light are provided, and
the control portion performs the operation in accordance with the comparison result of the comparing portion in the specific-light mode.

11. An endoscope apparatus comprising:
an illuminating-light supply portion which supplies illuminating light for irradiating a subject;
an image pick-up device which includes a charge amplifying mechanism for amplifying stored charges;
an amplifying portion which amplifies an image signal from the image pick-up device;

a light-amount control portion which adjusts the amount of light supplied to the subject by the illuminating-light supply portion;

a target setting portion which sets target value of the amplification of charges by the charge amplifying mechanism, of the amplification of the image signal by the amplifying portion, and of light-amount adjustment by the light-amount control portion;

a comparing portion which compares the amplitude of the image signal with comparison values based on the target values; and a control portion which controls the charge amplifying mechanism of the image pick-up device, the amplifying portion, and the light-amount control portion based on the comparison result of the comparing portion in a predetermined order.

12. An endoscope apparatus comprising:

an illuminating-light supply portion which supplies illuminating light for irradiating a subject;

an image pick-up device for picking-up an image of the subject, the image pick-up device being capable of amplifying stored charges therein;

an amplifying circuit which amplifies an image signal from the image pick-up device outside the image pick-up device; and a gain control portion which adjusts an amplification rate of the image signal to amplify the amplification of the image signal in a predetermined order inside and outside the image pick-up device so that the image of the subject displayed on the display means has a desired brightness.

13. An endoscope apparatus according to claim 12, further comprising:

an exposure-period control portion which controls an exposure time of the image pick-up device, wherein the gain control portion amplifies the image signal when the exposure time of the image pick-up device reaches a set upper value of the exposure time of the image pick-up device.

14. An endoscope apparatus according to claim 13, wherein the gain control portion amplifies the image signal by the amplification varied depending on wavelength bands of the illuminating light.

15. An image pick-up apparatus comprising:

an image pick-up device which picks-up an image of a subject;

a first-amplitude changing portion which changes an amplitude of an image signal from the image pick-up device by varying an exposure amount of the image pick-up device;

a second-amplitude changing portion which changes the amplitude of the image signal by varying an amplification rate of the image signal the image pick-up device;

a comparing portion which compares the amplitude of the image signal from the image pick-up device with a set comparison value;

a control portion which changes the amplitude of the image signal so as to be approximate to the set comparison value by controlling the first-amplitude changing portion or the second-amplitude changing portion in accordance with the comparison result of the comparing portion, the control portion preferentially controlling the amplitude of the image signal by any of the first-amplitude changing portion and the second-amplitude changing portion based on the noise level which is previously assumed to be generated in the amplitude control operation of the image signal by the first-amplitude changing portion and the noise level which is previously assumed to be generated in the amplitude control operation of the image signal by the second-amplitude changing portion, wherein the control portion first controls the first-amplitude changing portion that has a low influence on S/N ratio when increasing a brightness of an observed image of a subject displayed on a display means; and the control portion first controls the second-amplitude changing portion that has a high influence on S/N ration when decreasing the brightness of the observed image of the subject displayed on the display means.

16. An endoscope apparatus according to claim 11, wherein during the control portion operation to increase the amplitude of the image signal to be inputted to the display means and thereby increase a brightness of an observed image of the subject on the display means, based on the comparison result, the control portion controls the amplitude of the image signal in the following order: adjusting the amount of light by the light-amount control portion; amplifying the charges by the charge amplifying mechanism; and amplifying the image signal by the amplifying portion, and wherein during control portion operation to reduce the amplitude of the image signal inputted to the display means and thereby decrease the brightness of the observed image of the subject displayed on the display means, the control portion varies the amplitude of the image signal in the following order: amplifying the image signal by the amplifying portion; amplifying the charges by the charge amplifying mechanism; and adjusting the amount of light by the light-amount control portion.

17. An endoscope apparatus according to claim 12, wherein during gain control portion operation to increase the amplitude of the image signal to be inputted to the display means and thereby increase a brightness of an observed image of the subject on the display means, based on the comparison result, the gain control portion controls the amplitude of the image signal in the following order: amplifying the stored charges inside the image pick-up device; and amplifying the image signal by the amplifying portion, and wherein during gain control portion operation to reduce the amplitude of the image signal inputted to the display means and thereby decrease the brightness of the observed image of the subject displayed on the display means, the gain control portion varies the amplitude of the image signal in the following order: amplifying the image signal by the amplifying circuit; amplifying the stored charges inside the image pick-up device.

* * * * *